United States Patent
Ehr et al.

(10) Patent No.: US 7,722,412 B2
(45) Date of Patent: *May 25, 2010

(54) RETURN PAD CABLE CONNECTOR

(75) Inventors: Chris J. Ehr, Longmont, CO (US); Arthur Schoenman, Longmont, CO (US)

(73) Assignee: Covidien AG, Neuhausen Am Rheinfall (CH)

( * ) Notice: Subject to any disclaimer, the term of this patent is extended or adjusted under 35 U.S.C. 154(b) by 195 days.

This patent is subject to a terminal disclaimer.

(21) Appl. No.: 11/977,196

(22) Filed: Oct. 24, 2007

(65) Prior Publication Data

US 2008/0050984 A1 Feb. 28, 2008

Related U.S. Application Data

(60) Division of application No. 11/652,354, filed on Jan. 11, 2007, now Pat. No. 7,311,560, which is a continuation of application No. 10/478,343, filed as application No. PCT/US02/17360 on May 31, 2002, now Pat. No. 7,182,604.

(60) Provisional application No. 60/295,176, filed on Jun. 1, 2001.

(51) Int. Cl.
H01R 13/62 (2006.01)

(52) U.S. Cl. ............. 439/729; 439/909; 439/371; 600/372; 600/394; 607/152; 607/394; 128/908; 606/32; 606/35

(58) Field of Classification Search .......... 439/729, 439/909, 371, 828, 829, 483, 625; 600/372, 600/394; 607/152, 394; 128/908; 606/32, 606/35

See application file for complete search history.

(56) References Cited

U.S. PATENT DOCUMENTS

| 2,536,271 A | 1/1951 | Fransen et al. |
| 3,380,445 A | 4/1968 | Frasier |
| 3,534,306 A | 10/1970 | Watrous et al. |

(Continued)

FOREIGN PATENT DOCUMENTS

CA 1219642 3/1987

(Continued)

OTHER PUBLICATIONS

International Search Report EP 05021944.3 dated Jan. 25, 2006.

(Continued)

*Primary Examiner*—Gary F. Paumen

(57) ABSTRACT

A return pad cable connector, in accordance with the present disclosure, for use with a disposable return pad, includes a cord having a conductive wire disposed therethrough which conductive wire interconnects the return pad cable connector to an electrosurgical energy source. The return pad further includes a connector operatively coupled to the cord, the connector having a conductive surface which is selectively engageable with a corresponding conductive surface disposed on the return pad, the conductive surface of the connector including a conductive adhesive disposed thereon and a non-conductive adhesive disposed above the periphery of the conductive surface of the connector for engagement with a corresponding non-conductive adhesive disposed above the periphery of the conductive surface of the return pad. The connector can include a magnet for magnetically coupling the connector to the conductive surface disposed on the return pad.

16 Claims, 6 Drawing Sheets

U.S. PATENT DOCUMENTS

| | | |
|---|---|---|
| 3,543,760 A | 12/1970 | Bolduc |
| 3,642,008 A | 2/1972 | Bolduc |
| 3,683,923 A | 8/1972 | Anderson |
| 3,812,861 A | 5/1974 | Peters |
| 3,913,583 A | 10/1975 | Bross |
| 3,923,063 A | 12/1975 | Andrews et al. |
| 3,933,157 A | 1/1976 | Bjurwill et al. |
| 3,987,796 A | 10/1976 | Gonser |
| 4,067,342 A | 1/1978 | Burton |
| 4,092,985 A | 6/1978 | Kaufman |
| 4,094,320 A | 6/1978 | Newton et al. |
| 4,102,341 A | 7/1978 | Ikuno et al. |
| 4,114,622 A | 9/1978 | Gonser |
| 4,117,846 A | 10/1978 | Williams |
| 4,121,590 A | 10/1978 | Gonser |
| 4,126,137 A | 11/1978 | Archibald |
| 4,166,465 A | 9/1979 | Esty et al. |
| 4,188,927 A | 2/1980 | Harris |
| 4,200,104 A | 4/1980 | Harris |
| 4,200,105 A | 4/1980 | Gonser |
| 4,213,463 A | 7/1980 | Osenkarski |
| 4,231,372 A | 11/1980 | Newton |
| 4,237,887 A | 12/1980 | Gosner |
| 4,253,721 A | 3/1981 | Kaufman |
| 4,303,073 A | 12/1981 | Archibald |
| 4,304,235 A | 12/1981 | Kaufman |
| 4,331,149 A | 5/1982 | Gonser |
| 4,343,308 A | 8/1982 | Gross |
| 4,381,789 A | 5/1983 | Naser et al. |
| 4,384,582 A | 5/1983 | Watt |
| 4,387,714 A | 6/1983 | Geddes et al. |
| 4,393,584 A | 7/1983 | Bare et al. |
| 4,416,276 A | 11/1983 | Newton et al. |
| 4,416,277 A | 11/1983 | Newton et al. |
| 4,437,464 A | 3/1984 | Crow |
| 4,494,541 A | 1/1985 | Archibald |
| 4,643,193 A | 2/1987 | DeMarzo |
| 4,657,015 A | 4/1987 | Irnich |
| 4,658,819 A | 4/1987 | Harris et al. |
| 4,662,369 A | 5/1987 | Ensslin |
| 4,669,468 A | 6/1987 | Cartmell et al. |
| 4,699,146 A | 10/1987 | Sieverding |
| 4,722,761 A | 2/1988 | Cartmell et al. |
| 4,725,713 A | 2/1988 | Lehrke |
| 4,741,334 A | 5/1988 | Irnich |
| 4,745,918 A | 5/1988 | Feucht |
| 4,748,983 A | 6/1988 | Shigeta et al. |
| 4,750,482 A | 6/1988 | Sieverding |
| 4,754,757 A | 7/1988 | Feucht |
| 4,768,514 A | 9/1988 | DeMarzo |
| 4,770,173 A | 9/1988 | Feucht et al. |
| 4,788,977 A | 12/1988 | Farin et al. |
| 4,799,480 A | 1/1989 | Abraham et al. |
| 4,807,621 A | 2/1989 | Hagen et al. |
| 4,844,063 A | 7/1989 | Clark |
| 4,848,335 A | 7/1989 | Manes |
| 4,862,889 A | 9/1989 | Feucht |
| 4,873,974 A | 10/1989 | Hagen et al. |
| 4,895,169 A | 1/1990 | Heath |
| 4,942,313 A | 7/1990 | Kinzel |
| 4,947,846 A | 8/1990 | Kitagawa et al. |
| 4,955,381 A | 9/1990 | Way et al. |
| 4,961,047 A | 10/1990 | Carder |
| 4,969,885 A | 11/1990 | Farin |
| 5,000,753 A | 3/1991 | Hagen et al. |
| 5,004,425 A | 4/1991 | Hee |
| 5,010,896 A | 4/1991 | Westbrook |
| 5,038,796 A | 8/1991 | Axelgaard et al. |
| 5,042,981 A | 8/1991 | Gross |
| 5,061,914 A | 10/1991 | Busch et al. |
| 5,087,257 A | 2/1992 | Farin et al. |
| 5,114,424 A | 5/1992 | Hagen et al. |
| 5,152,762 A | 10/1992 | McElhenney |
| 5,160,334 A | 11/1992 | Billings et al. |
| 5,196,008 A | 3/1993 | Kuenecke et al. |
| 5,246,439 A | 9/1993 | Hebborn et al. |
| 5,271,417 A | 12/1993 | Swanson et al. |
| 5,276,079 A | 1/1994 | Duan et al. |
| 5,286,255 A | 2/1994 | Weber |
| 5,312,401 A | 5/1994 | Newton et al. |
| 5,336,255 A | 8/1994 | Kanare et al. |
| 5,352,315 A | 10/1994 | Carrier et al. |
| 5,362,420 A | 11/1994 | Itoh et al. |
| 5,370,645 A | 12/1994 | Klicek et al. |
| 5,385,679 A | 1/1995 | Uy et al. |
| 5,388,490 A | 2/1995 | Buck |
| 5,389,376 A | 2/1995 | Duan et al. |
| 5,390,382 A | 2/1995 | Hannant et al. |
| 5,409,966 A | 4/1995 | Duan et al. |
| 5,447,513 A | 9/1995 | Davison et al. |
| 5,449,365 A | 9/1995 | Green et al. |
| 5,452,725 A | 9/1995 | Martenson |
| 5,480,399 A | 1/1996 | Hebborn |
| 5,496,312 A | 3/1996 | Klicek |
| 5,496,363 A | 3/1996 | Burgio et al. |
| 5,520,180 A | 5/1996 | Uy et al. |
| 5,536,446 A | 7/1996 | Uy et al. |
| 5,540,684 A | 7/1996 | Hassler, Jr. |
| 5,599,347 A | 2/1997 | Hart et al. |
| 5,601,618 A | 2/1997 | James |
| 5,611,709 A | 3/1997 | McAnulty |
| 5,632,280 A | 5/1997 | Leyde et al. |
| 5,643,319 A | 7/1997 | Green et al. |
| 5,660,892 A | 8/1997 | Robbins et al. |
| 5,670,557 A | 9/1997 | Dietz et al. |
| 5,674,561 A | 10/1997 | Dietz et al. |
| 5,678,545 A | 10/1997 | Stratbucker |
| 5,688,269 A | 11/1997 | Newton et al. |
| 5,695,494 A | 12/1997 | Becker |
| 5,707,369 A | 1/1998 | Vaitekunas et al. |
| 5,718,719 A | 2/1998 | Clare et al. |
| 5,720,744 A | 2/1998 | Eggleston et al. |
| 5,766,165 A | 6/1998 | Gentelia et al. |
| 5,779,632 A | 7/1998 | Dietz et al. |
| 5,797,902 A | 8/1998 | Netherly |
| 5,800,426 A | 9/1998 | Taki et al. |
| 5,817,091 A | 10/1998 | Nardella et al. |
| 5,830,212 A | 11/1998 | Cartmell et al. |
| 5,836,942 A | 11/1998 | Netherly et al. |
| 5,846,558 A | 12/1998 | Nielsen et al. |
| 5,853,750 A | 12/1998 | Dietz et al. |
| 5,868,742 A | 2/1999 | Manes et al. |
| 5,924,983 A | 7/1999 | Takaki et al. |
| 5,947,961 A | 9/1999 | Netherly |
| 5,952,398 A | 9/1999 | Dietz et al. |
| 5,971,981 A | 10/1999 | Hill et al. |
| 5,976,128 A | 11/1999 | Schilling et al. |
| 5,985,990 A | 11/1999 | Kantner et al. |
| 5,999,061 A | 12/1999 | Pope et al. |
| 6,007,532 A | 12/1999 | Netherly |
| 6,010,054 A | 1/2000 | Johnson et al. |
| 6,030,381 A | 2/2000 | Jones et al. |
| 6,032,063 A | 2/2000 | Hoar et al. |
| 6,039,732 A | 3/2000 | Ichikawa et al. |
| 6,053,910 A | 4/2000 | Fleenor |
| RE36,720 E | 5/2000 | Green et al. |
| 6,059,778 A | 5/2000 | Sherman |
| 6,063,075 A | 5/2000 | Mihori |
| 6,083,221 A | 7/2000 | Fleenor et al. |
| 6,086,249 A | 7/2000 | Urich |
| 6,121,508 A | 9/2000 | Bischof et al. |
| 6,135,953 A | 10/2000 | Carim |
| 6,171,304 B1 | 1/2001 | Netherly et al. |
| 6,200,314 B1 | 3/2001 | Sherman |

| | | |
|---|---|---|
| 6,203,541 B1 | 3/2001 | Keppel |
| 6,214,000 B1 | 4/2001 | Fleenor et al. |
| 6,232,366 B1 | 5/2001 | Wang et al. |
| 6,240,323 B1 | 5/2001 | Calenzo, Sr. et al. |
| 6,258,085 B1 | 7/2001 | Eggleston |
| 6,275,786 B1 | 8/2001 | Daners |
| 6,301,500 B1 | 10/2001 | Van Herk et al. |
| 6,310,611 B1 | 10/2001 | Caldwell |
| 6,347,246 B1 | 2/2002 | Perrault et al. |
| 6,350,264 B1 | 2/2002 | Hooven |
| 6,357,089 B1 | 3/2002 | Koguchi et al. |
| 6,358,245 B1 | 3/2002 | Edwards et al. |
| 6,379,161 B1 | 4/2002 | Ma |
| 6,409,722 B1 | 6/2002 | Hoey et al. |
| 6,413,255 B1 | 7/2002 | Stern |
| 6,415,170 B1 | 7/2002 | Loutis et al. |
| 6,454,764 B1 | 9/2002 | Fleenor et al. |
| 6,488,678 B2 | 12/2002 | Sherman |
| 6,537,272 B2 | 3/2003 | Christopherson et al. |
| 6,544,258 B2 | 4/2003 | Fleenor et al. |
| 6,546,270 B1 | 4/2003 | Goldin et al. |
| 6,565,559 B2 | 5/2003 | Eggleston |
| 6,569,160 B1 | 5/2003 | Goldin et al. |
| 6,582,424 B2 | 6/2003 | Fleenor et al. |
| 6,666,859 B1 | 12/2003 | Fleenor et al. |
| 6,669,073 B2 | 12/2003 | Milliman et al. |
| 6,736,810 B2 | 5/2004 | Hoey et al. |
| 6,796,828 B2 | 9/2004 | Ehr et al. |
| 6,799,063 B2 | 9/2004 | Carson |
| 6,830,569 B2 | 12/2004 | Thompson et al. |
| 6,849,073 B2 | 2/2005 | Hoey et al. |
| 6,860,881 B2 | 3/2005 | Sturm |
| 6,875,210 B2 | 4/2005 | Refior et al. |
| 6,892,086 B2 | 5/2005 | Russell |
| 6,905,497 B2 | 6/2005 | Truckai et al. |
| 6,939,344 B2 | 9/2005 | Kreindel |
| 6,948,503 B2 | 9/2005 | Refior et al. |
| 6,953,139 B2 | 10/2005 | Milliman et al. |
| 6,959,852 B2 | 11/2005 | Shelton, IV et al. |
| 6,997,735 B2 | 2/2006 | Ehr et al. |
| 7,025,765 B2 | 4/2006 | Balbierz et al. |
| 7,128,253 B2 | 10/2006 | Mastri et al. |
| 7,143,926 B2 | 12/2006 | Shelton, IV et al. |
| 7,160,293 B2 | 1/2007 | Sturm et al. |
| 7,166,102 B2 | 1/2007 | Fleenor et al. |
| 7,169,144 B2 | 1/2007 | Hoey et al. |
| 7,169,145 B2 | 1/2007 | Isaacson et al. |
| 7,182,604 B2 | 2/2007 | Ehr et al. |
| 7,220,260 B2 | 5/2007 | Fleming et al. |
| 7,229,307 B2 | 6/2007 | Ehr et al. |
| 7,258,262 B2 | 8/2007 | Mastri et al. |
| 7,267,675 B2 | 9/2007 | Stern et al. |
| 7,278,562 B2 | 10/2007 | Mastri et al. |
| 7,303,107 B2 | 12/2007 | Milliman et al. |
| 7,308,998 B2 | 12/2007 | Mastri et al. |
| 7,311,560 B2 | 12/2007 | Ehr et al. |
| 7,357,287 B2 | 4/2008 | Shelton, IV et al. |
| 7,380,695 B2 | 6/2008 | Doll et al. |
| 7,422,589 B2 | 9/2008 | Newton et al. |
| 7,445,522 B2 * | 11/2008 | Burnes et al. ............... 439/725 |
| 7,473,145 B2 | 1/2009 | Ehr et al. |
| 2003/0139741 A1 | 7/2003 | Goble et al. |
| 2004/0150504 A1 | 8/2004 | Nicholson |
| 2005/0085806 A1 | 4/2005 | Auge, II et al. |
| 2005/0101947 A1 | 5/2005 | Jarrard et al. |
| 2005/0251130 A1 | 11/2005 | Boveja et al. |
| 2006/0041251 A1 | 2/2006 | Odell et al. |
| 2006/0041252 A1 | 2/2006 | Odell et al. |
| 2006/0041253 A1 | 2/2006 | Newton et al. |
| 2006/0074411 A1 | 4/2006 | Carmel et al. |
| 2006/0079872 A1 | 4/2006 | Eggleston |
| 2006/0173250 A1 | 8/2006 | Nessler |
| 2006/0217742 A1 | 9/2006 | Messerly et al. |
| 2006/0224150 A1 | 10/2006 | Arts et al. |
| 2007/0049914 A1 | 3/2007 | Eggleston |
| 2007/0049916 A1 | 3/2007 | Isaacson et al. |
| 2007/0049919 A1 | 3/2007 | Lee, Jr. et al. |
| 2007/0073284 A1 | 3/2007 | Sturm et al. |
| 2007/0074719 A1 | 4/2007 | Danek et al. |
| 2007/0161979 A1 | 7/2007 | McPherson |
| 2007/0167942 A1 | 7/2007 | Rick |
| 2007/0203481 A1 | 8/2007 | Gregg et al. |
| 2007/0244478 A1 | 10/2007 | Bahney |
| 2008/0009846 A1 | 1/2008 | Ward |
| 2008/0033276 A1 | 2/2008 | Ehr et al. |
| 2008/0083806 A1 | 4/2008 | Scirica |
| 2008/0083813 A1 | 4/2008 | Zemlok et al. |
| 2008/0249520 A1 | 10/2008 | Dunning et al. |
| 2008/0249524 A1 | 10/2008 | Dunning |
| 2008/0281309 A1 | 11/2008 | Dunning et al. |
| 2008/0281310 A1 | 11/2008 | Dunning et al. |
| 2008/0281311 A1 | 11/2008 | Dunning et al. |
| 2009/0036884 A1 | 2/2009 | Gregg et al. |
| 2009/0036885 A1 | 2/2009 | Gregg |

FOREIGN PATENT DOCUMENTS

| | | |
|---|---|---|
| DE | 3206947 | 9/1983 |
| DE | 3544443 | 6/1987 |
| DE | 42 38 263 A1 | 5/1993 |
| DE | 4231236 | 3/1994 |
| DE | 197 17 411 A1 | 11/1998 |
| DE | 198 01 173 | 7/1999 |
| DE | 103 28 514 | 6/2003 |
| DE | 102004010940 | 9/2005 |
| EP | 0262888 | 4/1988 |
| EP | 390937 | 10/1990 |
| EP | 836868 | 4/1998 |
| EP | 0 930 048 | 7/1999 |
| EP | 1 051 949 | 11/2000 |
| EP | 1076350 | 2/2001 |
| EP | 1 468 653 | 10/2004 |
| EP | 1 645 236 | 4/2006 |
| EP | 1707151 | 10/2006 |
| EP | 1 808 144 | 7/2007 |
| EP | 1902684 | 3/2008 |
| FR | 2276027 | 6/1974 |
| FR | 2516782 | 5/1983 |
| GB | 2 054 382 | 2/1981 |
| GB | 2374532 | 10/2002 |
| WO | WO 96/19152 | 6/1996 |
| WO | WO 97/37719 | 10/1997 |
| WO | WO 98/18395 | 5/1998 |
| WO | WO 98/53751 | 12/1998 |
| WO | WO 99/09899 | 3/1999 |
| WO | WO 99/11187 | 3/1999 |
| WO | WO 00/06246 | 2/2000 |
| WO | WO 00/32122 | 6/2000 |
| WO | WO 00/53113 | 9/2000 |
| WO | WO 00/65993 | 11/2000 |
| WO | WO 01/87175 | 11/2001 |
| WO | WO 02/058579 | 8/2002 |
| WO | WO 02/060526 | 8/2002 |
| WO | WO 02/099442 | 12/2002 |
| WO | WO 03/094766 | 11/2003 |
| WO | WO 2004/028385 | 4/2004 |
| WO | WO 2004/074854 | 9/2004 |
| WO | WO 2005/048809 | 6/2005 |
| WO | WO 2005/087124 | 9/2005 |
| WO | WO 2005/099606 | 10/2005 |
| WO | WO 2005/110263 | 11/2005 |

| WO | WO 2005/115262 | 12/2005 |
| WO | WO 2008/009385 | 1/2008 |

OTHER PUBLICATIONS

International Search Report EP 05002027.0 dated May 12, 2005.
International Search Report EP 06006961 dated Aug. 3, 2006.
International Search Report EP 07000885.9 dated May 15, 2007.
International Search Report PCT/US2004/004196 dated Oct. 4, 2007.
International Search Report EP06006961.4 dated Oct. 5, 2007.
International Search Report EP07000885.9 dated May 2, 2007.
International Search Report EP07007783.9 dated Aug. 6, 2007.
International Search Report EP06018206.0 dated Oct. 13, 2006.
International Search Report EP07000567.3 dated Dec. 3, 2008.
International Search Report EP08006731 dated Jul. 14, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
Boyles, Walt; "Instrumentation Reference Book", 2002; Butterworth-Heinemann ; 262-264.
International Search Report EP06023756.7 dated Feb. 21, 2008.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.

* cited by examiner

RETURN PAD CABLE CONNECTOR

CROSS-REFERENCE TO RELATED APPLICATION

The present application is a Divisional Application that claims the benefit of and priority to U.S. application Ser. No. 11/652,354, filed Jan. 11, 2007 now U.S. Pat. No. 7,311,560, which is a Continuation Application application Ser. No. 10/478,343 that claims the benefit of and priority to U.S. Pat. No. 7,182,604, filed Nov. 19, 2003 now U.S. Pat. No. 7,182,604, which claims the benefit of and priority to International Application Serial No. PCT/US02/17360, filed May 31, 2002, which claims the benefit of and priority to U.S. Provisional Application Ser. No. 60/295,176, filed Jun. 1, 2001, the entire contents of each of which being incorporated herein by reference.

BACKGROUND

1. Technical Field

The present disclosure relates to a return pad cable connector and, more particularly, to a return pad cable connector having a reusable cable configuration and adapted to removably receive a disposable single use patient return pad.

2. Background of Related Art

Flexible conductive members (i.e., return pads, return electrodes, etc.) are of particular importance in the medical community wherein patients often need to be connected to electrical monitoring or electrical generating equipment. In such applications, flexible conductive members such as return pads or electrodes need to adapt to the shape of the patient's body in order to provide sufficient electrical contact with the surface of the patient's body.

Electrosurgery requires that an electrosurgical generator be connected to at least two electrodes to produce and deliver an electrical potential to a patient's body. For example, in monopolar electrosurgery, the electrodes usually consist of an active electrode applied at the surgical site and a return electrode or pad applied to a non-surgical site on the patient.

Generally, return electrodes are pliable and thus can be flexed or shaped to meet particular application requirements. Return electrodes are usually manufactured to attach with a pressure sensitive adhesive directly to the surface of the patient's body. Return electrodes are therefore designed and manufactured to be form fitting or flexible so as to provide adequate conductive contact with the non-flat surfaces of a patient's body. Typically a conductive adhesive is applied to the surface of the return electrode to hold and secure the return electrode to the patient's body.

The return electrodes need to be electrically connected to the source electrosurgical generator. This connection is usually provided by way of one or more insulated conductive wires which are configured to interface with the electrosurgical generator to complete the electrosurgical circuit. In the past, emphasis was placed on providing a tight physical connection between the conductive wire and the return electrode which could withstand potential disengagement of the conductive wire and return pad during a surgical procedure.

Contemporary wire termination and connection methods usually require that the ends of a wire be stripped of insulation, formed, and assembled to the flexible conductive member with a staple shaped attachment or some other attachable fastener such as a circular terminal and a rivet. The stripping process is highly dependent upon the nature of the insulation of the wire, the strip tooling design, and the tooling setup. Wire stripping problems can result in broken wire strands or wires that cannot be formed or terminated properly in subsequent operations. As can be appreciated, existing terminating and connection manufacturing processes tend to be overly complex and typically require tedious manufacturing steps to assure adequate electrical and mechanical connections. Inadequate electrical connections can result in impedance changes across the tissue which may effect the performance of the overall electrosurgical system.

In addition, for sanitary and medical reasons, after a return electrode (i.e., return pad) has been used in a medical procedure for a particular patient, the return pad is discarded and a new return pad is used for a new medical procedure for either the same or a different patient. Since return pads of the prior art are usually physically coupled to the conductive wire (i.e., hard wired), the conductive portion and generation leads are discarded along with the return pad. Typically, only the return pad needs to be discarded after each medical procedure for sanitary reasons. Disposal of both the return pad and the conductive portion simply increases the costs associated with the medical procedure.

Accordingly, the need exists for a return pad/electrode cable connector which incorporates a disposable return pad which is removably coupled to a reusable conductive portion/connector.

SUMMARY

A return pad cable connector, in accordance with the present disclosure, for use with a disposable return pad, includes a cord having a conductive wire disposed therethrough which conductive wire interconnects the return pad cable connector to an electrosurgical energy source. The return pad further includes a connector operatively coupled to the cord, the connector having a conductive surface which is selectively engageable with a corresponding conductive surface disposed on the return pad, the conductive surface of the connector including a conductive adhesive disposed thereon and a non-conductive adhesive disposed above the periphery of the conductive surface of the connector for engagement with a corresponding non-conductive adhesive disposed above the periphery of the conductive surface of the return pad.

In still yet another embodiment, according to the present disclosure the cord-to-pad connector includes a base element having a handle and a fixed jaw having a conductive surface affixed to an inner surface thereof. A distal end of the conductive wire passes through the base element and operatively engages the conductive surface of the fixed jaw. The cord-to-pad connector further includes a return pad clamp pivotally mounted to the base element. The cord-to-pad connector is positionable between an open position wherein the return pad clamp is spaced from the fixed jaw and a closed position wherein the return pad clamp is in contact with the fixed jaw. Preferably, the return pad clamp includes a moveable jaw and a clamping lever depending therefrom and extending along the handle which allows a user to selectively engage and disengage a return pad.

Preferably, the cord-to-pad connector further includes a locking mechanism configured and adapted to selectively maintain the cord-to-pad connector in the closed position. The locking mechanism includes a latch projecting from the clamping lever of the return pad clamp and a locking rail projecting from a locking aperture formed in the handle. In use, the latch operatively engages the locking rail, thereby locking the cord-to-pad connector in the closed position.

Preferably, the return pad includes a pad-to-cord connector which has a conductive pad surface disposed thereon which conductive pad surface is configured and adapted to operatively engage the conductive surface of the base element. In this manner, an electrical connection between the return pad and the cord-to-pad connector is established. A conductive adhesive may be disposed between the conductive pad surface and the conductive surface of the base element to facilitate the electrical connection and to maintain electrical continuity between elements.

In an alternative embodiment, the return pad cable connector of the present disclosure includes a cord having a conductive wire disposed therethrough which connects to an electrosurgical energy source and a connector which operatively couples to the cord wherein the connector has at least one magnet disposed thereon for magnetically coupling the connector to a conductive surface disposed on the return pad. In accordance with the present disclosure, when the connector is magnetically coupled to the conductive surface disposed on the return pad energy is permitted to pass from the return pad to the electrosurgical energy source via the conductive wire.

Preferably, the at least one magnet is made from an electrically conductive material. More preferably, the conductive wire of the cord is electrically coupled to the at least one electrically conductive magnet.

In an alternative embodiment, the connector further includes at least one electrical contact disposed on the surface of at least one of the magnets. Preferably, the conductive wire of the cord is electrically coupled to each of the at least one electrical contact.

In still an alternative embodiment, the connector includes a flexible substrate having a first portion and a second portion integrally connected to the first portion, the first and second portion defining a fold line therebetween and a magnet disposed on each of the first and second portions of the flexible substrate in order to sandwich the conductive surface of the return pad therebetween. Preferably, the conductive wire of the cord is electrically coupled to the magnet, such that when the connector is magnetically coupled to the conductive surface disposed on the return pad, energy is permitted to pass from the return pad to the electrosurgical energy source via the conductive wire.

It is envisioned that at least the magnet which is electrically coupled to the conductive wire is made from an electrically conductive material. Preferably, the connector further includes at least one electrical contact disposed on the surface of the magnet which is electrically coupled to the conductive wire. The conductive wire of the cord is preferably electrically coupled to each of the at least one electrical contacts.

It is envisioned that the conductive wire of the cord can extend from a side of the substrate which is either parallel to the fold line or transverse to the fold line. It is further envisioned that each magnet is coupled to the substrate via a pin passing through the magnet and into the substrate.

These and other advantages and features of the apparatus disclosed herein, will become apparent through reference to the following description of embodiments, the accompanying drawings and the claims.

DESCRIPTION OF THE DRAWINGS

The accompanying drawings, which are incorporated in and constitute a part of this specification, illustrate embodiments of the invention and, together with a general description of the invention given above, and the description of the embodiments given below, serve to explain the principles of the invention.

DETAILED DESCRIPTION

Figure 1:
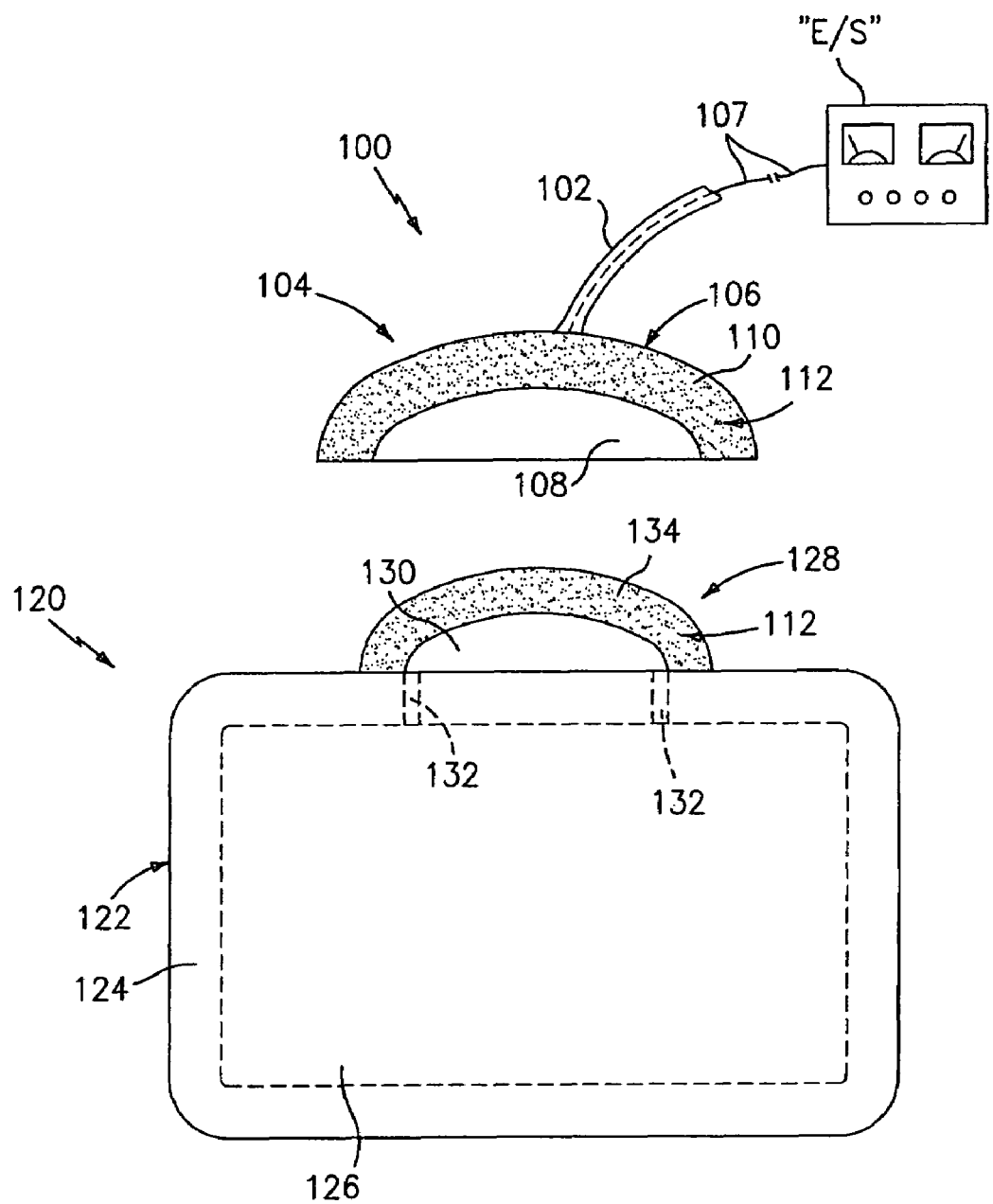
FIG. 1 is a bottom plan view of a return pad and an electrode cable connector in accordance with the present disclosure.

Preferred embodiments of the presently disclosed return pad cable connector will now be described in detail with reference to the drawing figures wherein like reference numerals identify similar or identical elements.

Referring now in detail to FIG. 1, a return pad cable connector is shown in accordance with the present disclosure and is generally identified as 100. Cable connector 100 includes a reusable conductive wire cable 102 which operatively couples at a proximal end thereof to an electrosurgical generator "E/S" and a reusable cord-to-pad interface 104 which is disposed at a distal end thereof. Cord-to-pad interface 104 includes an insulated backing 106 having a conductive cord surface 108 disposed thereon which electrically couples to a wire 107 passing through cable 102.

An adhesive border 110 is defined about the outer periphery of the conductive cord surface 108. It is contemplated that conductive cord surface 108 may be positioned along one edge of cord-to-pad interface 104 to facilitate connection with the return pad 120. However, it is also envisioned that the conductive cord surface 108 or multiple conductive cord surfaces 108 may be arranged anywhere on the surface of the cord-to-pad interface 104 defending upon a particular purpose or to facilitate electrical engagement. Preferably, the adhesive border 110 includes a non-conductive adhesive 112 applied thereto which reduces stray electrical current from emanating from the conductive cord surface 108.

As seen in FIG. 1, cable connector 100 is configured and adapted to be removably adhered to a return pad or return electrode 120. Return pad 120 includes an insulated backing 122, an insulated cover 124 and a conventional electrically conductive member 126 retained between insulated backing 122 and insulated cover 124.

Insulated backing 122 includes a pad-to-cord interface 128 which extends from a side surface thereof. Pad-to-cord interface 128 includes a conductive pad surface 130, preferably made from an electrically conductive material, disposed thereon which electrically couples return pad 120 to the conductive cord surface 108. Conductive pad surface 130 is electrically connected to conductive member 126 (via at least one conductive wire 132 which is disposed between backing 122 and cover 124). An adhesive border 134 is defined about the outer periphery of the conductive cord surface 108. It is contemplated that conductive pad surface 130 is positioned to compliment the particular arrangements of conductive surface(s) 108 on the cord-to-pad interfaces. Much like adhesive border 110, adhesive border 134 may also include a non-conductive adhesive 112 applied thereto to facilitate engagement and reduce stray electrical currents.

A non-conductive adhesive for adhering adhesive border 110 of cord-to-pad interface 104 to adhesive border 134 of pad-to-cord interface 128 is disclosed in commonly owned U.S. Pat. No. 4,699,146 to Sieverding, the entire contents of which are incorporated herein by reference. By providing cord-to-pad interface 104 with an adhesive border 110 and providing pad-to-cord interface 128 with an adhesive border 134, sufficient electrical connection is established between conductive cord surface 108 and conductive pad surface 130. More particularly, cord-to-pad interface 104 is adhered to pad-to-cord interface 128 by applying the non-conductive adhesive 112 to their respective adhesive borders 110 and 134 and pressing the two interfaces together. In this manner, conductive cord surface 108 directly contacts conductive pad surface 130 thereby establishing an electrical connection therebetween.

Figure 2:
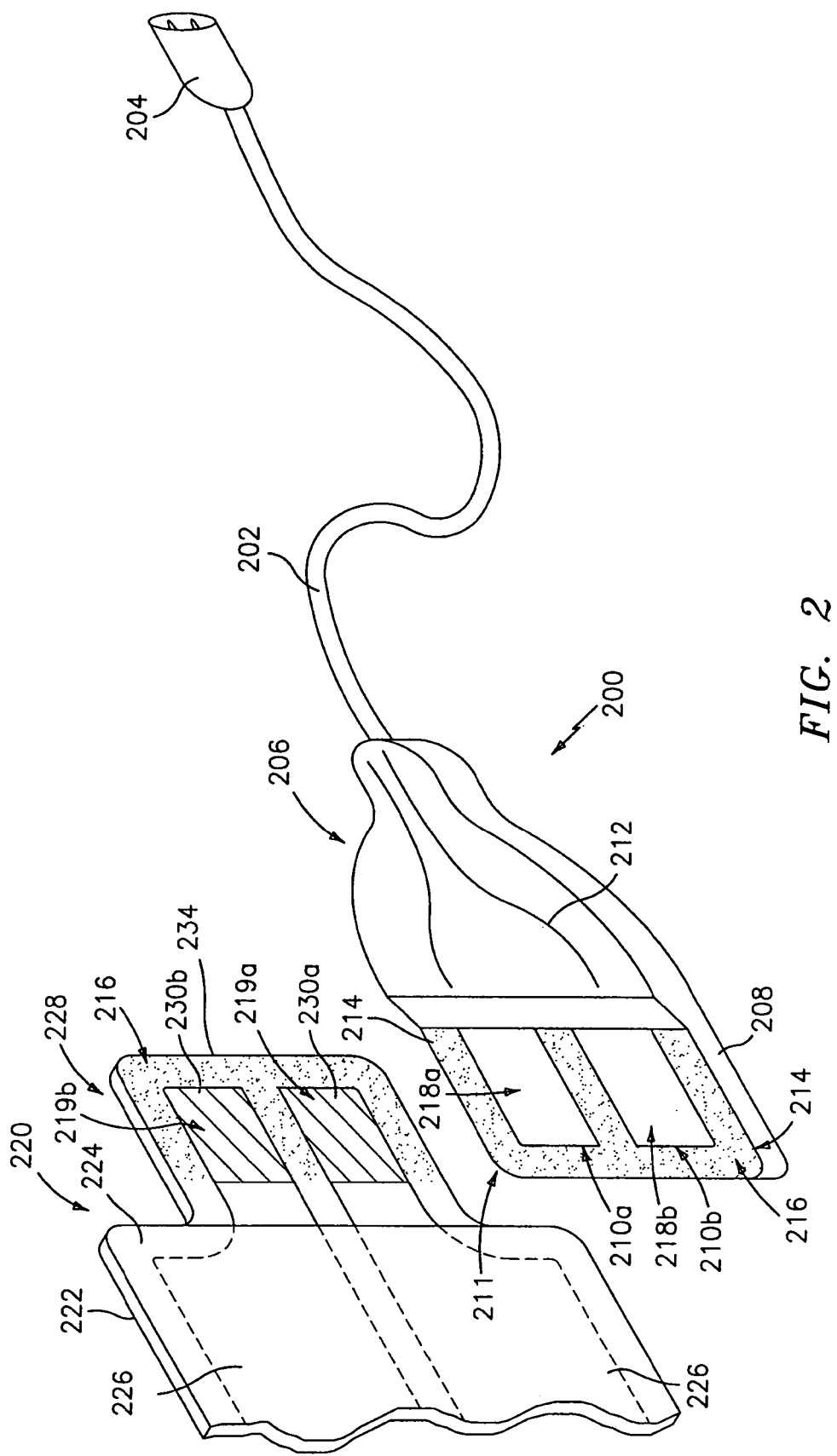
FIG. 2 is a perspective view of a return pad and an electrode cable connector in accordance with an alternative embodiment of the present disclosure.
Figure 3:
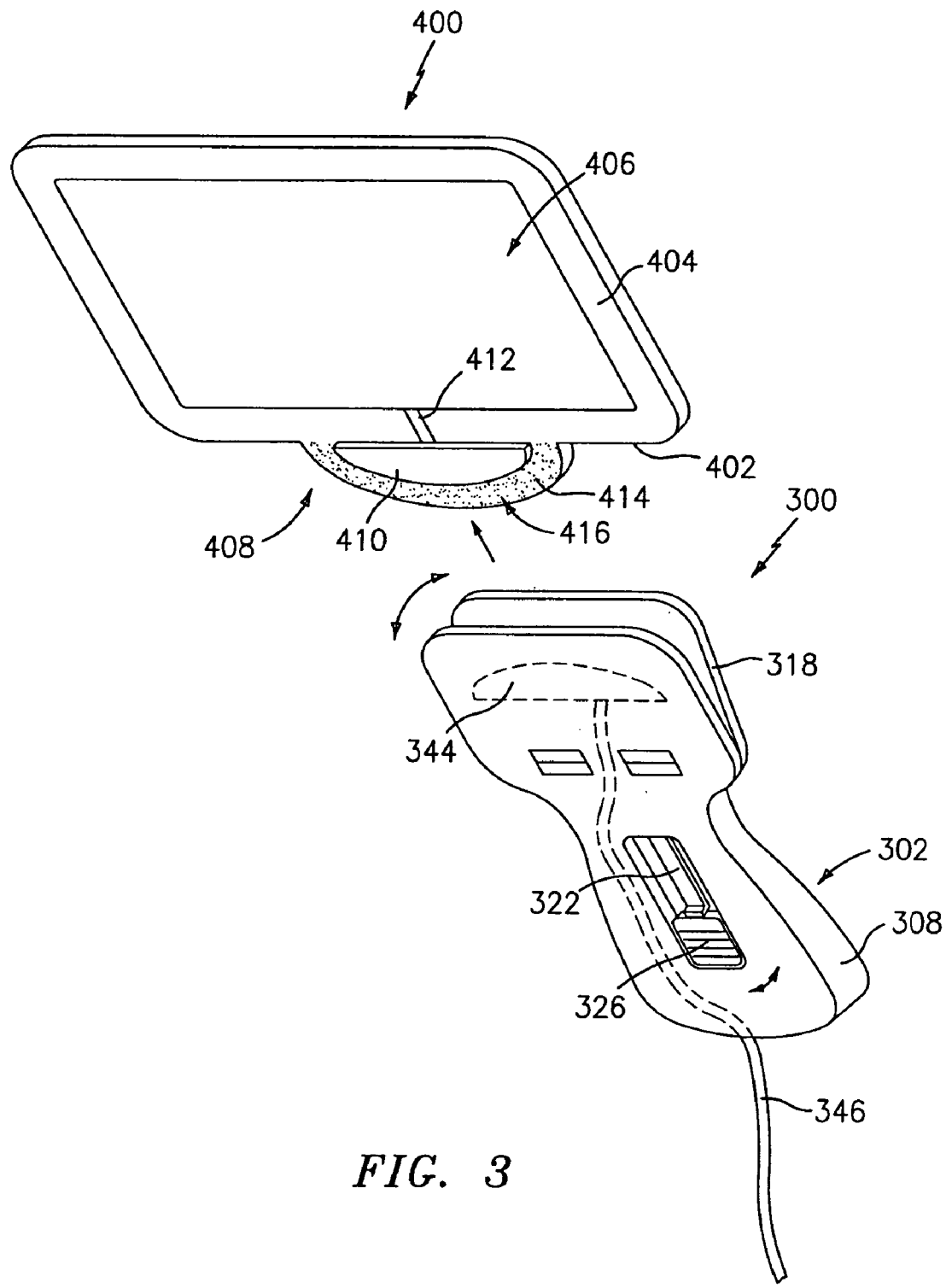
FIG. 3 is a perspective view of a return pad and an electrode cable connector in accordance with yet another embodiment of the present disclosure.

Turning now to FIG. 2, a return pad cable connector is shown in accordance with another embodiment of the present disclosure and is generally identified as cable connector 200. Cable connector 200 includes a reusable conductive wire cable 202 having a typical connector 204 attached to a proximal end thereof for interfacing cable 202 with an electrosurgical generator (not shown) and a reusable cord-to-pad interface 206 operatively coupled to a distal end thereof. Cord-to-pad interface 206 includes an insulated backing 208 having a pair of conductive cord surfaces 210a, 210b disposed thereon which electrically couple to a wire 212 passing through cable 202.

Conductive cord surfaces 210a, 210b are preferably spaced from one another and extend distally along a top surface 211 of cord-to-pad interface 206. An adhesive border 214 is defined about the periphery of each conductive cord surface 210a, 210b. Adhesive border 214 may include a non-conductive adhesive 216 applied thereto in order to facilitate mechanical connection with return pad 220. A conductive adhesive 218a, 281b is applied to each conductive cord surface 210a, 210b, respectively.

As seen in FIG. 2, cable connector 200 is configured and adapted to be removably adhered to return pad 220. Return pad 220 is similar to return pad 120 of FIG. 1 but includes a pair of complimentary conductive surfaces 230a, 230b which electrically couple with conductive pad surfaces 210a, 210b, respectively. Each conductive surface 230a, 230b, in turn, is coupled to a conductive member 236a, 236b disposed within the return pad 220.

More particularly, return pad 220 includes an insulated backing 222 having a pad-to-cord interface 228 which extends from a side surface thereof. Pad-to-cord interface 228 includes the pad conductive surfaces 230a, 230b disposed thereon which couple with conductive cord surfaces 210a, 210b. An adhesive border 234 surrounds the periphery of each conductive pad surface 230. Adhesive border 234 is configured to include a non-conductive adhesive 216 applied thereto which reduces stray current which may emanate from the conductive surfaces. A conductive adhesive 218 and covers each conductive pad surface 230a, 230b to facilitate and maintain electrical connection with conductive cord surfaces 210a, 210b.

Preferably, a conductive adhesive 218 is selected such that the conductivity of the adhesive will be sufficient for the electrosurgical power to be conducted through the small area of the attachment as well as provide impedance low enough for contact quality monitoring in the generator. While a non-conductive and a conductive adhesive have been contemplated for use in the present embodiment, it is envisioned that a single conductive adhesive can be applied to both adhesive borders 214 and 234 as well as to both conductive surfaces 210a, 210b and 230a, 230b. Adhesive 218a, 218b is selected such that the electro-conductivity of the adhesive promotes the transfer of electric signals between conductive surfaces 210a, 210b and 230a, 230b.

Turning now to FIGS. 3-6, a return pad cable connector is shown in accordance with another embodiment of the present disclosure and is generally identified as 300. Cable connector 300 includes two major subunits; a base element 302 and a return pad clamp 304 (see FIG. 4). As explained in greater detail below, base element 302 and return pad clamp 304 cooperate to grip the return pad 400. It is contemplated that both base element 302 and return pad clamp 304 are preferably molded from a strong, resilient plastic material, such as acetal resin.

Base element 302 includes a return pad interface 306 and a handle 308. Preferably, handle 308 is dimensioned to facilitate gripping and may be ergonomically shaped to enhance "feel".

Return pad interface 306 preferably includes a fixed jaw 312 having an L-shaped cross-section defined by a first leg 310 for housing a series of pivot mounts 336 disposed therein and a second leg 311 which vertically extends therefrom which cooperates with the pad clamp 304 to secure the return pad 400 as explained in more detail below. A lever housing 314 is formed in the pad interface 306 and operates to mechanically align and secure the pad clamp 304 with handle 308. More particularly, a locking aperture 316 extends through handle 308 and is located toward the distal end of the same (308). As explained in more detail below, locking aperture 316 and lever housing 314 cooperate to align and secure the pad clamp 304 within handle 308.

Return pad clamp 304 includes a movable jaw 318 and a clamping lever 320 which depends from movable jaw 318 and which is designed to mechanically engage handle 308. Clamping lever 320 includes a proximal half 322 having an offset 324 which extends at an angle relative to proximal half 322. A distal half 326 depends from offset 324 such that proximal half 322, offset 324 and distal half 326 form a generally reverse "S" configuration which facilitates assembly of the cable connector 300. In other words, the proximal and distal halves 322 and 326 are generally parallel to one another and offset 324 is disposed perpendicular thereto. Movable jaw 318 also includes a series of pivot projections 334 which are designed for mechanical engagement with pivot mounts 336 as discussed below.

A locking pivot grip 328 is disposed on the proximal half 322 of the return pad clamp 304 and a corresponding unlocking pivot grip 330 is formed on the distal half 326. The locking and unlocking pivot grips 328 and 330 are designed to facilitate movement of clamping lever 320 by an operator's finger to mechanically move/pivot jaw member 318 from a first open position for reception of the return pad 400 to the second locking position which secures the return pad 400 in electro-mechanical engagement with the cable connector 300.

Return pad clamp 304 is pivotally mounted to base element 302 so that movable jaw 318 lies in registration with fixed jaw 312 and pivots about an axis "A" (see FIGS. 5 and 6) defined through first leg 310 of the return pad interface 306. More particularly, the return pad clamp 304 is mounted by passing clamping lever 320 through lever housing 314 and engaging the pivot projections 334 within the corresponding pivot mounts 336 disposed in first leg 310.

Clamping lever 320 when mounted extends along handle 308, preferably lying in a channel 338 defined therein. More particularly, clamping lever 320, when mounted, extends through lever housing 314 and to locking aperture 316 such that the distal half 326 is movable within locking aperture 316 from a first locking position wherein movable jaw is secured to the return pad 400 (see FIG. 5) to a second open position for disengaging the return pad 400 (see FIG. 6). Preferably, locking aperture 316 is designed to accept and cooperate with clamping lever 320 in the manner described above. For example, in one embodiment, locking aperture 316 is generally keyhole shaped, with a rectangular portion designed to accommodate distal half 326 of clamping lever 320, and a circular, chamfered thumb well 340 which surrounds unlocking grip 330. The length of offset 324 is preferably dimensioned to allow proximal half 322 to lie generally flush with the outer surface of handle 308 when clamping lever 320 is disposed in the "locked" position. Also, when locked, distal half 326 is generally flush with the opposite surface of handle 308.

Figure 5:
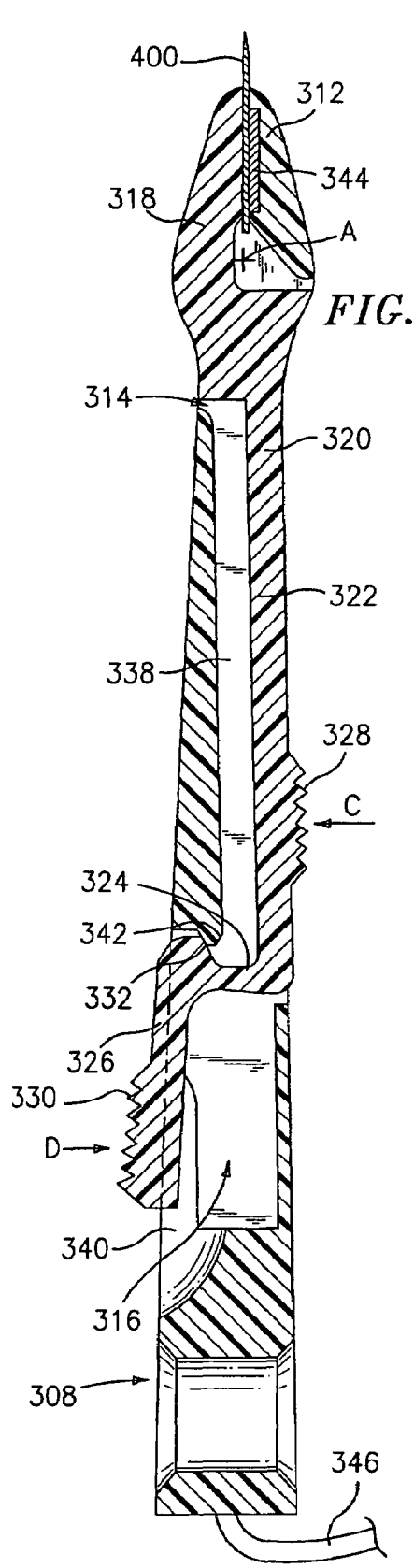
FIG. 5 is a cross-sectional side elevational view of the electrode connector of FIG. 4 shown in the closed position.

A locking rail 342 is disposed within locking aperture 316 and is designed to mechanically engage a corresponding latch 332 disposed on offset 324 to secure clamping lever 320 in a "locked" position which, in turn, locks the cable connector 300 to the return pad 400. As can be appreciated, cooperation between locking rail 342 and latch 332 is made possible by dimensioning clamping lever 320 such that the distance from axis A to the tip of latch 332 is slightly less than the distance from that point to the tip of locking rail 342. Thus, when the unit is in a locked position, as shown in FIG. 5, latch 332 is securely retained by locking rail 342. As described in more detail below, movement of distal half 326 via un-locking grip 330 in direction "D" disengages latch 332 from locking rail 342 which, in turn, disengages/unlocks the clamping lever 320 and releases the return pad 400.

Figure 4:
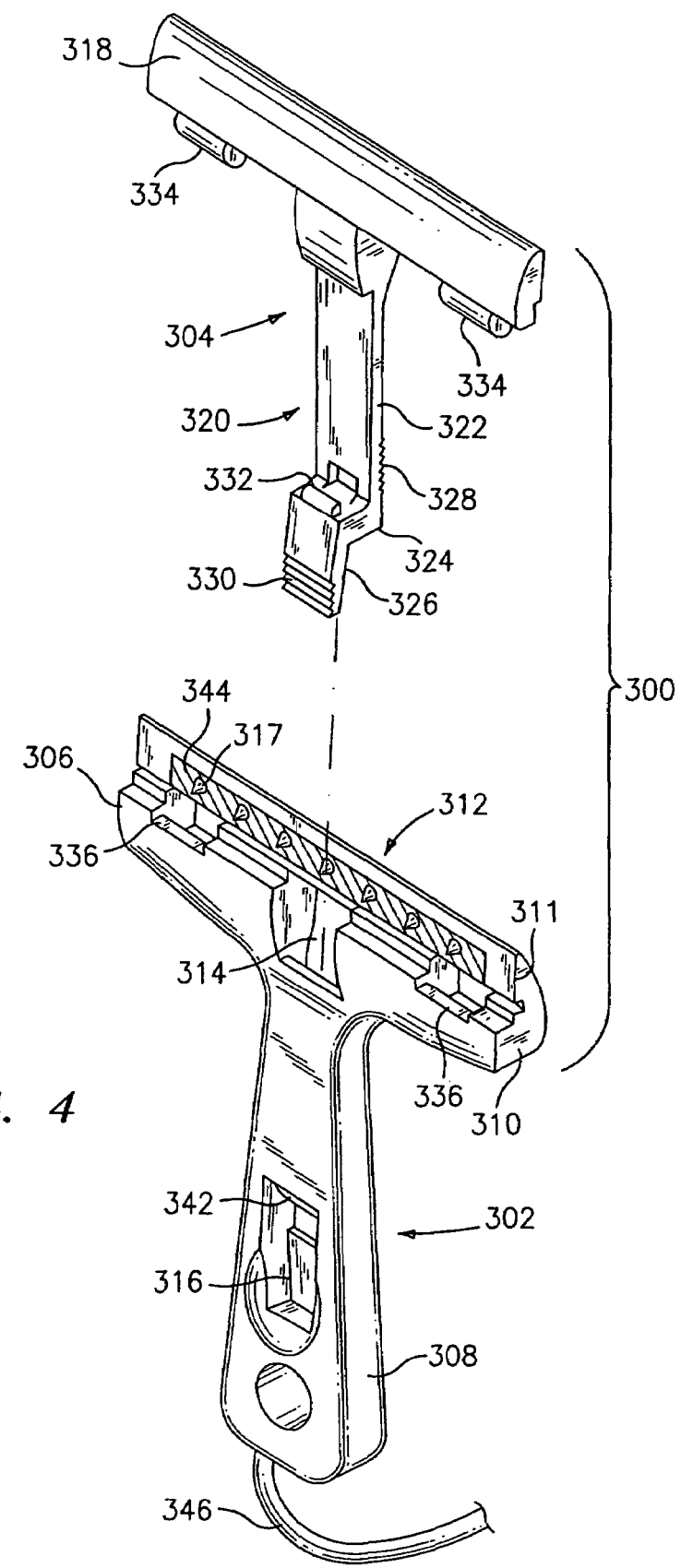
FIG. 4 is an exploded, perspective view of a return pad and an electrode cable connector similar to the embodiments shown in FIG. 3.

As best shown in FIG. 4, base element 302 also includes a conductive surface 344 affixed to an inner facing surface of fixed jaw 312 which couples with a conductive wire 346 extending from handle 308 to the electrosurgical generator (not shown).

Returning to FIG. 3, cable connector 300 is configured and adapted to be removably coupled to return pad 400. Return pad 400 includes an insulated backing 402, an insulated cover 404 and a conventional electrically conductive member 406 retained between insulated backing 402 and insulated cover 404.

Insulated backing 402 includes a pad-to-cord connector 408 extending from a side surface thereof. Pad-to-cord connector 408 includes a conductive pad surface 410 disposed thereon for electrically connecting return pad 400 to conductive surface 344 of connector 300. Conductive pad surface 410 is electrically connected to conductive member 406 via a conductive path 412. An adhesive border 414 surrounds conductive pad surface 410 and is configured such that a non-conductive adhesive 416 can be applied thereto. It is contemplated that a conductive adhesive can be applied between conductive surface 344 of connector 300 and pad conductive surface 410 to assure electrical continuity between the same.

As seen in FIG. 5, while in a locked position connector 300 firmly holds return pad 400 between fixed and movable jaws 312 and 318, respectively, via the mechanically cooperative action of latch 332 and locking rail 342. In this manner, conductive surface 344 of connector 300 and conductive pad surface 410 of return pad 400 are held in electrical contact with one another. In the open position, as shown in FIG. 6, movable jaw 318 is rotated away from fixed jaw 312, permitting insertion and removal of return pad 400 therefrom.

Figure 6:
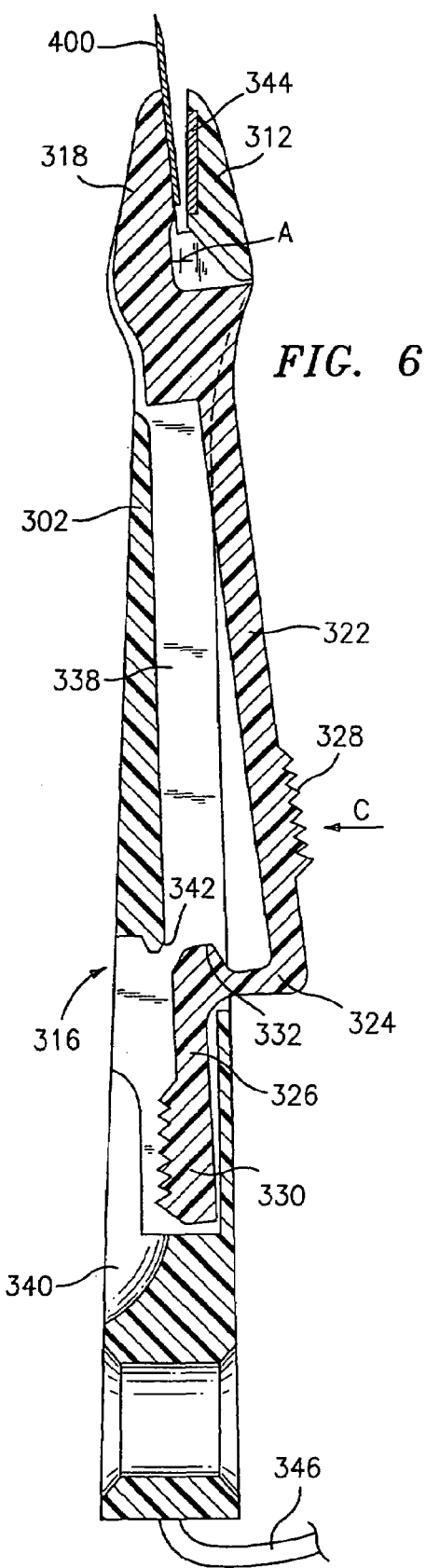
FIG. 6 is a cross-sectional side elevational view of the electrode connector of FIG. 4 shown in the open position.

Movement between the open and the closed/locked positions is shown in FIGS. 5 and 6. To move from the closed/locked position (as seen in FIG. 5), the operator applies a force in the direction "D" to unlocking grip 330, preferably by pressing with a thumb or finger. By applying a force in the direction "D" the distal half 326 and latch 332 unlocks causing the movable jaw 318 of clamping member 320 to pivot away from fixed jaw 312 and release pad 400. In turn, offset 324 rotates upward, forcing the proximal half 322 out of channel 338. More particularly, applying a force in the direction "D" rotates the pivot projections 334 within pivot mounts 336 to cause movable jaw 318 to open. Once rotated to the "open" position, the return pad 400 is either released or a new return pad may be positioned therein.

Once the return pad 400 is in place between the movable jaw 318 and the fixed jaw 312, the connector 300 can be locked. Locking of connector 300 involves applying a force in a direction "C" to locking grip 328. This forces latch 332 against locking rail 342, causing proximate leg 322 to flex and rotate latch 332 beyond locking rail 342 thus moving clamp lever 320 to a "locked" position (see FIG. 5). In turn, the pivot projections of moveable jaw 318 are rotated within pivot mounts 336 of fixed jaw 316 thereby securing return pad 400 between the jaw members 312, 318.

In accordance with the present disclosure, it is envisioned that each jaw member 312, 318 may be provided with a plurality of teeth 317 formed on either conductive surface 344 of connector 300, the non-conductive surface of second leg 311 of fixed jaw 312 or both. Accordingly, the plurality of teeth 317 increases the retention of pad-to-chord connector 408 of return pad 400 therebetween.

Turning now to FIGS. 7-10 a return pad cable connector in shown in accordance with the principles of the present disclosure and is generally identified as 500. In accordance with the present disclosure it is envisioned that return pad cable connector 500 is configured and adapted to cooperate with a return electrode 120 as generally described above.

Figure 7:
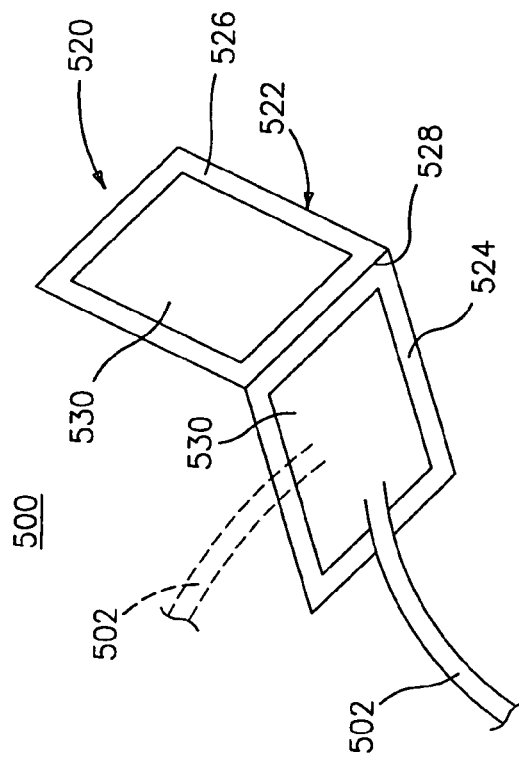
FIG. 7 is a top plan view of an electrode cable connector in accordance with an alternative embodiment of the present disclosure.

With particular reference to FIG. 7, return pad cable connector 500 includes a conductive return wire cable 502, operatively coupled at a proximal end thereof to an electrosurgical generator (not shown), and a cord-to-pad interface 504 operatively coupled to a distal end thereof. In accordance with the present disclosure, it is envisioned that cord-to-pad interface 504 is made of an electrically conductive magnetic material. Accordingly, when cord-to-pad interface 504 is approximated toward or brought into contact with conductive pad surface 130 of return pad 120, interface 504 will magnetically couple with conductive-pad surface 130. As such, the contact between cord-to-pad interface 504 and conductive pad surface 130 will return energy during electrosurgical procedures, from return pad 120 to the electrosurgical generator (not shown).

Figure 8:
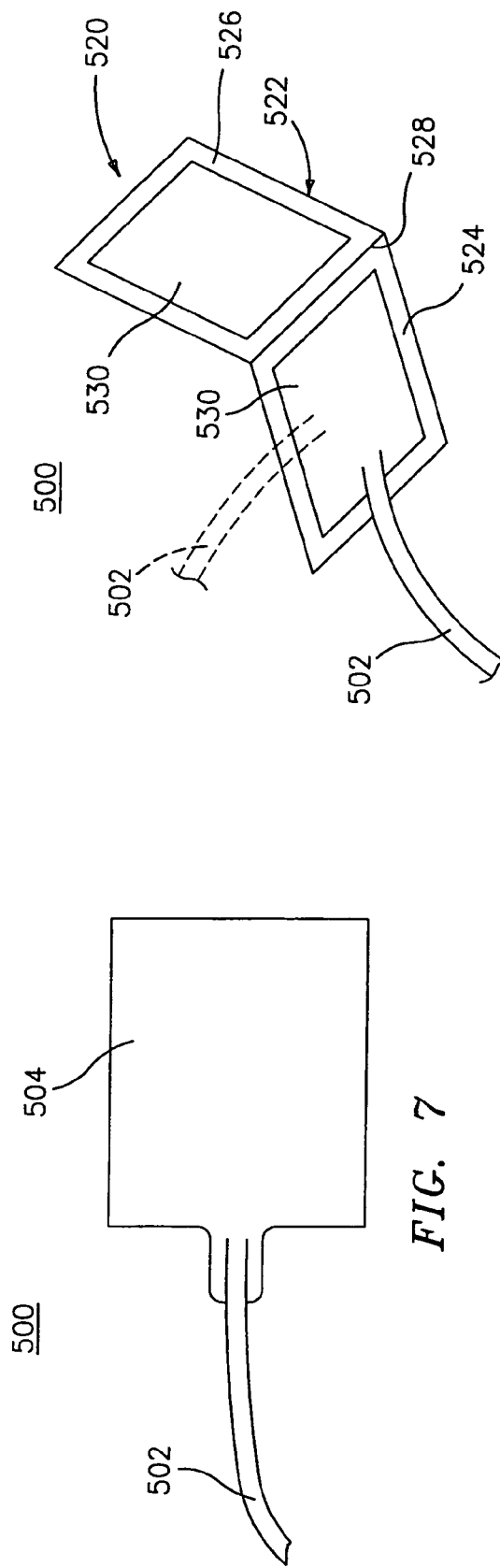
FIG. 8 is a top plan view of an electrode cable connector in accordance with yet another embodiment of the present disclosure.

Turning now to FIG. 8, return pad cable connector 500 includes a conductive return wire cable 502, operatively coupled at a proximal end thereof to an electrosurgical generator (not shown), and a cord-to-pad interface 510 operatively coupled to a distal end thereof. In accordance with the present embodiment, cord-to-pad interface 510 includes a magnetic substrate 512 having at least one electrical contact 514 disposed thereon, wherein wire cable 502 is electrically coupled to electrical contact(s) 514. It is envisioned that magnetic substrate 512 can be made from either conductive or non-conductive materials. Accordingly, when cord-to-pad interface 510 is approximated toward or brought into contact with conductive pad surface 130 of return pad 120, such that the at least one electrical contact 514 will be brought into contact with conductive pad surface 130, interface 510 will magnetically couple with conductive pad surface 130. As such, the contact between cord-to-pad interface 510 and conductive pad surface 130 will return energy during electrosurgical procedures, from return pad 120 to the electrosurgical generator (not shown).

Figure 9:
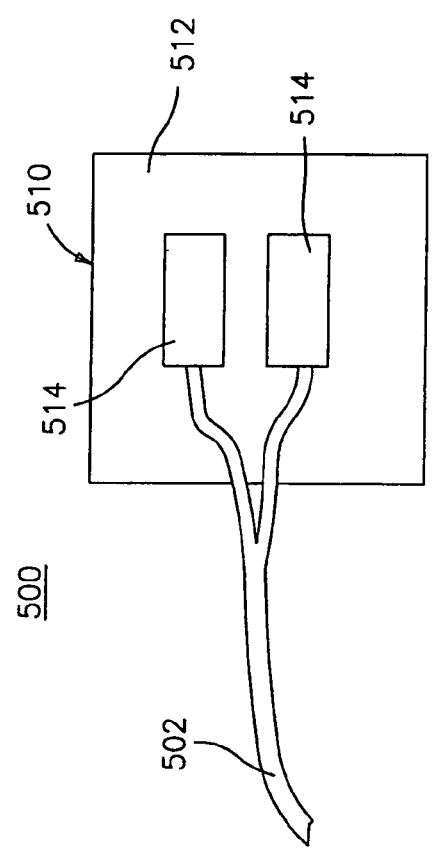
FIG. 9 is a perspective view of an electrode cable connector in accordance with still another embodiment of the present disclosure.

Turning now to FIG. 9, return pad cable connector 500 includes a conductive return wire cable 502, operatively coupled at a proximal end thereof to an electrosurgical generator (not shown), and a cord-to-pad interface 520 operatively coupled to a distal end thereof. Cord-to-pad interface 520 includes a flexible substrate 522 having a first portion 524 and a second portion 526 integrally connected to first portion 524 to thereby define a fold line 528. Cord-to-pad interface 520 further includes an electrically conductive magnet 530 provided on each of first and second portions 524, 526 of substrate 522, wherein wire cable 502 is electrically coupled to one of the pair of magnets 530. While a pair of electrically conductive magnets 530 is disclosed, it is contemplated that only magnet 530, which is electrically coupled to wire cable 502, needs to be made from an electrically conductive material while the other magnet can be made from non-conductive materials. It is further envisioned that, if both magnets 530 are non-conductive, an electrical contact (not shown) can be disposed on magnet 530 which is electrical contact is electrically coupled to wire cable 502.

As seen in FIG. 9, wire cable 502 can extend from return pad cable connector 500 from a side of substrate 522 which is parallel to fold line 528, or in the alternative, as shown in phantom, wire cable 502 can extend from return pad cable connector 500 from a side of substrate 522 which is transverse to fold line 528.

Use of return pad cable connector 500, shown in FIG. 9, requires that after conductive pad surface 130 of return pad 120 is brought into contact with magnet 530 with is electrically coupled to wire cable 502, flexible substrate 522 is folded along fold line 528 in order to approximate magnets 530 of first and second portions 524, 526 toward one another thereby sandwiching conductive pad surface 130 therebetween. As such, the contact between magnet 530, coupled to-wire cable 502, and conductive pad surface 130 will return energy during electrosurgical procedures, from return pad 120 to the electrosurgical generator (not shown).

Figure 10:
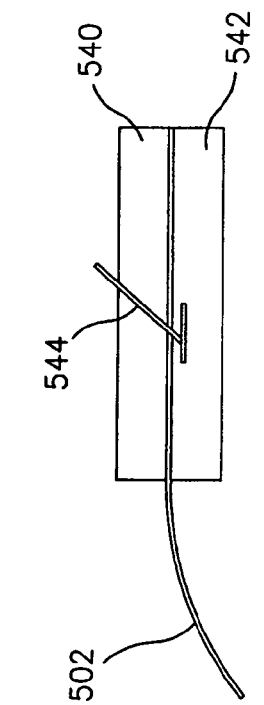
FIG. 10 is a side elevational view of an electrode cable connector of FIG. 9 illustrating a preferred method of coupling of a magnet to a substrate thereof.

As seen in FIG. 10, a preferred method of coupling a magnet to a substrate for a return pad cable connector 500 is illustrated. In particular, a magnet 540 overlies a substrate 542 and at least one retaining device 544 (i.e., a pin) is used to pass though magnet 540 and imbedded in substrate 542 to secure magnet 540 to substrate 542. Further, as seen in FIG. 10, wire cable 502 can be disposed between magnet 540 and substrate 542. While a pin has been disclosed it is envisioned that other methods of coupling the magnet to a substrate can be used, such as, for example, an adhesive, screws, clips, clamps and the like.

The use of magnets in return pad cable connector 500 results in easier attachment and removal of return pad cable connector 500 from conductive pad surface 130 of return pad 120 as well as easier cleaning of the contact surfaces and a lower profile.

In accordance with the present disclosure, it is envisioned that return pad cable connector 500 can be used in combination with a conductive adhesive disposed between return pad cable connector 500 and conductive pad surface 130.

The above description should not be construed as limiting, but merely as exemplifications of preferred embodiments. Those skilled in the art will envision other modifications within the scope and spirit of the present disclosure.

What is claimed is:

1. A return pad cable connector for use with a disposable return pad, the cable connector comprising:
   a cord having a conductive wire disposed therethrough which connects to an electrosurgical energy source;
   a connector which operatively couples to the cord, the connector having:
      at least two conductive cord surfaces, each of the at least two conductive cord surfaces being selectively engagable with a corresponding conductive return pad surface disposed on the return pad, and at least one of the conductive cord surfaces of the connector including a conductive hdhesive disposed thereon; and
   a non-conductive adhesive disposed about the periphery of at least one of the at least two conductive cord surfaces of the connector for engagement with a corresponding non-conductive adhesive disposed about the periphery of at least one of the conductive return pad surfaces of the return pad.

2. The return pad cable connector of claim 1, wherein each conductive cord surface of the connector includes conductive adhesive disposed thereon and wherein each conductive cord surface of the connector includes a non-conductive adhesive disposed about their periphery.

3. The return pad cable device of claim 1, wherein the connector includes a base element and a return pad clamp, the return pad clamp being pivotally mounted to the base element.

4. The return pad cable device of claim 1, wherein the connector includes a locking mechanism adapted to selectively maintain the connector in a desired position.

5. The return pad cable device of claim 1, wherein the connector is configured to electrically couple a return pad to an electrosurgical generator.

6. A return pad cable device, comprising:
   a connector having at least two conductive cord surfaces, each of the at least two conductive cord surfaces being configured to correspondingly mate with a respective conductive return pad surface of a return pad;
   at least one conductive adhesive disposed on at least a portion of the connector; and
   at least one non-conductive adhesive disposed on at least another portion of the connector.

7. The return pad cable device of claim 6, wherein the at least one conductive adhesive is disposed on at least one of the conductive cord surfaces of the connector.

8. The return pad cable device of claim 6, wherein the at least one non-conductive adhesive is disposed about the periphery of at least one of the conductive cord surfaces of the connector.

9. The return pad cable device of claim 6, wherein the connector includes a base element and a return pad clamp, the return pad clamp being pivotally mounted to the base element.

10. The return pad cable device of claim 6, wherein the connector further includes a locking mechanism adapted to selectively maintain the connector in a desired position.

11. An electrosurgical system, comprising:
a cord adapted to connect to a source of electrosurgical energy;
a return pad operatively connectable to the cord and having at least two conductive return pad surfaces; and
a connector operatively coupled to the cord and which is engagable with the return pad, the connector including at least two conductive cord surfaces, each of the at least two conductive cord surfaces being configured to mate with at least one conductive return pad surface, and the connector including at least one conductive adhesive and at least one non-conductive adhesive disposed thereon.

12. The electrosurgical system of claim 11, further including at least one non-conductive adhesive disposed on a portion of the return pad.

13. The electrosurgical system of claim 11, further including at least one non-conductive adhesive disposed about a periphery of at least one of the conductive return pad surfaces of the return pad.

14. The electrosurgical system of claim 11, wherein the at least one conductive adhesive is disposed on at least one of the conductive cord surfaces of the connector.

15. The electrosurgical system of claim 11, wherein the at least one non-conductive adhesive is disposed about the periphery of at least one of the conductive cord surfaces of the connector.

16. A return pad cable device, comprising:
a connector having at least two conductive cord surfaces, each of the at least two conductive cord surfaces being configured to correspondingly mate with a respective conductive return pad surface of a return pad, the connector configured to electrically couple a return pad to an electrosurgical generator;
at least one conductive adhesive disposed on at least a portion of the connector; and
at least one non-conductive adhesive disposed on at least another portion of the connector.

* * * * *